United States Patent [19] [11] 3,987,204
Monti [45] Oct. 19, 1976

[54] DIRECT COMPRESSION VEHICLE

[75] Inventor: Anthony Monti, Irvington, N.Y.

[73] Assignee: SuCrest Corporation, New York, N.Y.

[22] Filed: Apr. 24, 1975

[21] Appl. No.: 571,234

Related U.S. Application Data

[60] Division of Ser. No. 289,545, Sept. 15, 1972, Pat. No. 3,900,569, which is a continuation-in-part of Ser. No. 185,344, Sept. 30, 1971, Pat. No. 3,821,414, which is a continuation of Ser. No. 885,980, Dec. 17, 1969, abandoned.

[52] U.S. Cl. ............................................. 424/361
[51] Int. Cl.² .......................................... A61K 47/00
[58] Field of Search ................................... 424/361

[56] References Cited
UNITED STATES PATENTS

| | | | |
|---|---|---|---|
| 3,042,668 | 7/1962 | Monti et al. ........................ | 260/209 |
| 3,134,719 | 5/1964 | Sheth et al. ...................... | 424/361 X |
| 3,424,842 | 1/1969 | Nurnberg ......................... | 424/361 X |
| 3,639,168 | 1/1972 | Monti et al. ..................... | 424/361 X |
| 3,639,169 | 1/1972 | Broeg et al. ..................... | 424/361 X |
| 3,821,414 | 6/1974 | Monti ............................. | 424/361 |

*Primary Examiner*—Shep K. Rose
*Attorney, Agent, or Firm*—Kenyon & Kenyon, et al

[57] ABSTRACT

An intimate, co-dried mixture of a major amount of tricalcium phosphate and a minor amount of locust bean gum is useful for the preparation of tablets by the direction compression technique. The mixture is blended with an active material and, if desired, fillers, disintegrating agents and lubricants, and the resulting blend is compressed without prior granulation or slugging to form a tablet containing at least about 10 weight per cent of the co-dried mixture.

1 Claim, No Drawings

DIRECT COMPRESSION VEHICLE

This application is a division of application Ser. No. 289,545 filed Sept. 15, 1972, now U.S. Pat. No. 3,900,569; which was a continuation-in-part of application Ser. No. 185,344 filed Sept. 30, 1971, now U.S. Pat. No. 3,821,414; which in turn was a continuation of Ser. No. 885,980, filed Dec. 17, 1969, and now abandoned.

This invention relates to direct compression vehicles. More particularly, this invention relates to a particulate composition which can be admixed with an active material and, optionally, fillers, disintegrating agents and lubricants, and the resulting mixture directly compressed into a tablet without the necessity of granulation or slugging of the mixture.

There are two general methods for forming tablets, i.e. compression of a dry particulate material and trituration, or molding of a moist material, of which the first technique is by far the most frequently employed. The compression technique may be further subdivided into three major categories, viz. direct compression, wet granulation and dry granulation. The direct compression technique is the most desirable, in that it employs the fewest steps and, in the case of the production of tablets containing sensitive or unstable actives, such as certain pharmaceuticals, minimizes the exposure to water or other conditions tending to adversely affect stability of the active. Unfortunately, however, it has been found that the direct compression technique is of limited applicability.

First, most active materials possess poor compression properties, and thus are unsuited to this technique. In addition, many actives are required in such small amounts per unit dosage form that direct compression of the active alone is impractical, if not impossible. As a result, the active must be admixed with a direct compression vehicle, i.e., an inert composition which is compatible with the active and has good compressibility. In addition, the direct compression vehicle should have good flowability, good stability under normal ambient conditions, no adverse effect on tablet disintegration time, the ability to produce good tablet surfaces, and low cost.

To date, however, no material has been found which satisfies all of these criteria. For example, of the most popular of such compression vehicles, spray-dried lactose possesses poor stability and discolors on storing, dicalcium phosphate provides tablets having poor strength and high abrasiveness, and microcrystalline cellulose is expensive.

It is an object of the present invention to provide a new direct compression vehicle.

It is a further object of this invention to provide a direct compression vehicle which may be combined with an active, and, if desired, fillers, disintegrating agents and lubricants, and the resulting dry mixture subjected to direct compression.

The direct compression vehicles of the present invention are an intimate, co-dried admixture of a minor portion of locust bean gum and a major portion of tricalcium phosphate. Neither locust bean gum nor tricalcium phosphate is useful as a direct compression vehicle because neither can be compressed into a tablet of adequate strength. It is surprising then, that a co-dried mixture of these materials is so useful.

By the term "major portion" is meant a portion greater than about 50 weight per cent, and by the term "minor portion" is meant a portion less than about 50 weight per cent. The minimum effective amount of locust bean gum is not narrowly critical, provided that the resulting tablet has the desired strength characteristics, which also depend upon the active component and other materials, e.g., fillers, disintegrating agents and lubricants, which may be incorporated with the co-dried mixture which is compressed into the tablet. In general, however, the direct compression vehicle of this invention should contain at least about 0.5 weight per cent, and preferably at least about 1 weight per cent, locust bean gum. Tablet strength increases with increasing proportions of locust bean gum, but ordinarily amounts in excess of about 20 or 30 weight per cent are unnecessary. Higher proportions can be employed, but there is no corresponding improvement in tablet strength and, because locust bean gum is considerably more expensive than tricalcium phosphate, are not desirable from an economic standpoint. Amounts of locust bean gum in the range of from about 1 to about 10 weight per cent are preferred, with an amount of about 5 weight per cent being particularly preferred.

The co-dried mixture is obtained by forming an aqueous suspension or dispersion of locust bean gum and tricalcium phosphate in the desired proportions, drying the aqueous mixture and reducing the dried product to a particulate composition of the desired size.

To obtain the desired beneficial effects, it has been found that a more intimate mixture than that obtained by dry blending is necessary. Accordingly, the locust bean gum and tricalcium phosphate are mixed in an aqueous medium. The amount of water is not narrowly critical, provided that the resulting aqueous dispersion is sufficiently fluid to permit mixing. In general, this requires that there be at least 25 parts water per part locust bean gum, with amounts of at least 50 parts water per part locust bean gum being preferred. The maximum amount of water is in no way critical, but amounts in excess of 200 parts per part of locust bean gum are unnecessary and only increase drying time and/or heat requirements and may preclude some drying techniques, such as drum drying, which requires a relatively viscous liquid. In general, amounts of from about 50 to about 150 parts of water per part of locust bean gum are employed.

The water, locust bean gum and tricalcium phosphate can be combined simultaneously, or in any order. In a preferred technique, however, locust bean gum is added to the water and the resulting mixture thoroughly stirred to form a clear sol of hydrated gum in water. Then the tricalcium phosphate is stirred in. Because tricalcium phosphate is only very slightly soluble in water, it is preferably added in a finely divided form to ensure that it is uniformly dispersed throughout the locust bean gum. In general, the particle size should be below about 100-mesh, and particle sizes in the range of from about 200- to about 325-mesh are preferred.

Drying of the resulting dispersion may be effected by a variety of techniques, such as spray drying, tray drying, drum drying, and the like.

The dried product is then broken up into particles having the desired dimensions and, if necessary, screened to achieve the proper size range and distribution. To ensure good flowability it is desired that the particles be larger than 120 mesh, and preferably be in the range of from 40 to 80 mesh. The resulting particulate product comprises minute particles of the tricalcium phosphate dispersed throughout a locust bean gum matrix, and is substantially different in appearance and properties from mixtures of the same dry materials obtained by blending or the wet granulation technique.

The particulate direct compression vehicle of this invention is admixed with the active which it is desired to incorporate into tablet form and, if desired, other common tablet components such as fillers, disintegrating agents and lubricants, and the mixture is tabletted by known direct compression procedures. The proportions of vehicle, actives, fillers, distintegrating agents and lubricants, are not critical, and obviously depend upon the active material and the unit dose desired in the tablet, as well as the properties desired in the tablet. In general, however, the direct compression vehicle can comprise at least 10 per cent of the tabletting mixture, and may comprise as much as 99.9 per cent by weight, although amounts in the range of from about 30 to about 95 per cent are more common.

By the term "active material" is meant any material intended for ingestion having a beneficial or desirable effect on the user. Suitable active materials include therapeutic materials, such as anesthetics, antibiotics, anti-tussives, vitamins, aspirin, antacids, and the like; food stuffs, such as cocoa, dried oats, fruit flakes and the like; edible dyes and other food additives; and so on. The vehicle is a free-flowing granular material and imparts improved flow characteristics to the active material and other components of the blend, thereby assuring ease of tabletting.

The blend of direct compression vehicle, active material and other additives is mixed and directly compressed to form a tablet employing conventional techniques and apparatus.

Although the co-dried mixture is useful as a direct compression vehicle, it has been found desirable to modify it by blending it with other materials prior to use as a direct compression vehicle.

For example, the co-dried composition can be diluted with granular tricalcium phosphate without serious reduction of tablet strength. By the term "granular", as employed herein, is meant a product having particle sizes in excess of about 120 mesh, and preferably in excess of 60 to 70 mesh. A suitable granular tricalcium phosphate is disclosed in U.S. Pat. No. 3,134,719. The amount of tricalcium phosphate employed is not narrowly critical, but it should not be so high as to materially reduce the tablet strength afforded by the co-dried blend, and in general the weight of granular tricalcium phosphate should not be greater than twice the weight of the co-dried blend.

Although the presence of tricalcium phosphate in amounts of up to about 2 times the amount of co-dried blend does not materially affect tablet strength, it has been found that as the proportion of co-dried blend decreases the incidence of "picking", i.e. the accumulation of material on the die punch, increases. This can be minimized through the use of lubricants, such as magnesium stearate. However, as the amount of lubricant in increased above about 0.75 per cent, there is a serious loss of tablet strength and the dispersibility of the resulting tablet in water is materially retarded. To minimize the need for lubricants, the co-dried blend can be admixed with locust bean gum, which tends to act both as a lubricating and as a disintegrating agent. The effective amount of locust bean gum is not highly critical, and ordinarily will be about 5 to about 15 weight per cent, based upon the co-dried blend. When granular tricalcium phosphate is present, the locust bean gum ordinarily will be employed in an amount of from about 3 to about 7 percent, based upon the combined weight of co-dried blend and granular tricalcium phosphate.

In some instances, the locust bean gum is unable to impart a desired disintegration rate. In such cases, it has been found desirable to employ a pharmaceutically acceptable acidic material as an auxilliary disintegration agent. The combination of locust bean gum and acidic material provides higher disintegration rates than are obtained with either material alone. The acidic material can be an organic acid, such as citric acid, aspirin, adipic acid, fumaric acid, succinic acid, malic acid or tartaric acid, with citric acid and tartaric acid being preferred, or it can be a salt of a weak base and a strong acid, such as ferrous sulfate, aluminum sulfate or monocalcium phosphate, with monocalcium phosphate being preferred. Citric acid is especially preferred. The amount of acidic material is not highly critical, provided it is sufficient to impart the desired disintegration rate. In general, amounts of from about 1 to about 7 weight per cent, based upon co-dried blend, and from about 1 to about 3 weight per cent, based upon combined co-dried blend and granular tricalcium phosphate have been found useful.

The acidic material can be admixed with the co-dried blend in any suitable fashion. To assure uniform distribution, however, it has been found desirable to first admix the acidic material with a diluent, preferably tricalcium phosphate, and pulverize the mixture to form a powder, i.e. a particulate material having particle sizes of less than 120 mesh, and preferably less than 150 to 250 mesh. The powder is then admixed with co-dried blend and, if employed, the granular tricalcium phosphate. The ratio or acicic material to diluent in the powder is not highly critical, and approximately equal parts by weight (i.e. 40 to 60 weight per cent acidic material and 60 to 40 weight per cent diluent) are satisfactory.

In accordance with this invention, a particularly preferred direct compression vehicle comprises a dry, physical admixture of:

a. From about 30 to about 90 parts by weight of the co-dried mixture of locust bean gum and tricalcium phosphate of this invention, as described above;

b. Up to about 60 parts by weight of granular tricalcium phosphate, the combined weight of co-dried mixture and granular tricalcium phosphate being from about 90 to about 95 parts by weight;

c. From about 3 to about 7 parts by weight of locust bean gum; and d. From about 2 to about 5 parts by weight of a powdered blend of approximately equal parts by weight of tricalcium phosphate and an acidic material, especially citric acid.

The following examples are illustrative. Unless otherwise specified, all parts and percentages are by weight.

EXAMPLE I

A 10-gram portion of locust bean gum was added to 1000 cc. water and the resulting mixture thoroughly stirred. Then 90 grams of tricalcium phosphate was added and thoroughly mixed to yield a creamy white suspension. The suspension was drum dried to yield a free-flowing powder, which was formed into a 13/32 inch, 0.5 gram tablet at 4500 psi. The ejection pressure needed to eject the tablets from the die was from 100 to 150 psi and the Stokes hardness of the tablets was in excess of 45.

When disodium phosphate or calcium chloride were substituted for the tricalcium phosphate, tablets having a Stokes hardness of only 18 were obtained.

EXAMPLE II

A 30-gram portion of locust bean gum was added to 1000 cc. water and stirred to form a viscous mixture. Then 70 grams of tricalcium phosphate was added, followed by 300 cc. and 200 cc. portions of water, with mixing to yield a homogenous milky suspension. After drum drying and tabletting as described in Example I, the ejection pressure was 40 psi and the Stokes hardness was 45.

EXAMPLE III

Employing procedures similar to those described in Example I, except that the suspension was oven dried at 60° C., compositions containing from 0 to 7 weight per cent locust bean gum and 93 to 100 weight per cent tricalcium phosphate were produced and formed into tablets. The Stokes hardness and dispersibility were measured and are summarized as follows:

| Tablet Composition, wt.% | | Product Properties | |
|---|---|---|---|
| Locust Bean Gum | Calcium Phosphate | Hardness | Dispersibility* |
| 0 | 100 | 11 | 15 min. |
| 0 | 100 | 13 | |
| 1 | 99 | 27 | 1 min. |
| 1 | 99 | 24 | |
| 5 | 95 | 43 | 3 min. |
| 5 | 95 | 40.5 | |
| 7 | 93 | 39 | 4½ min. |
| 7 | 93 | 37.5 | |

*Time to disperse in 10 cc. of water in closed test tube which was inverted at a rate of 30 times per minute.

EXAMPLE IV

A series of tabletting mixtures was prepared using locust bean gum, tricalcium phosphate and two co-dried mixtures of locust bean gum and tricalcium phosphate containing 3 or 5% of locust bean gum. Each of the resulting mixtures was used to prepare 13/32-inch tablets on a Carver press at 4500 pounds pressure for 10 seconds and the tablets were evaluated for Stokes hardness and capping. The data for these experiments is summarized as follows:

| Component | Blend No. | | | |
|---|---|---|---|---|
| | 1 | 2 | 3 | 4 |
| Locust bean gum, % | 5 | 5 | 4.5 | 5 |
| Tricalcium phosphate, % | 95 | 85 | 65.5 | 45 |
| Co-dried blend (3% locust bean gum), % | — | — | — | 50 |
| Co-dried blend (5% locust bean gum), % | — | 10 | 30 | |
| Stokes Hardness, kg | 28.5 | 31.5 | 32.6 | 34.1 |
| Capping | Sev. | Mod. | None | None |

From the above data it is evident that increased amounts of the co-dried blend afforded improved tablet strength and reduced the incidence of capping.

EXAMPLE V

A mixture of 5 parts locust bean gum, 45 parts tricalcium phosphate and 50 parts of a co-dried mixture of tricalcium phosphate and locust bean gum containing 3% locust bean gum was prepared and admixed with magnesium stearate and varying amounts of citric acid. The resulting tabletting mixtures were formed into tablets and the disintegration time of the tablets was determined by the standard U.S.P. disintegration test. The data for these experiments are summarized as follows:

| | Experiment No. | | | |
|---|---|---|---|---|
| | 1 | 2 | 3 | 4 |
| Mixture, % | 99 | 2 | 94 | 89 |
| Magnesium stearate, % | 1 | 1 | 1 | 1 |
| Citric Acid, % | — | 1 | 5 | 10 |
| Disintegration time, min. | >30 | 2½ | 1¼ | 1¼ |

EXAMPLE VI

A series of experiments was performed in which co-dried locust bean gum-tricalcium phosphate blends were admixed with locust bean gum, magnesium stearate and monocalcium phosphate, the mixtures were employed to form tablets, and the tablets were evaluated for disintegration time. The data from these experiments are summarized as follows:

| Mixture Composition | Run No. | | | | | |
|---|---|---|---|---|---|---|
| | 1 | 2 | 3 | 4 | 5 | 6 |
| Blend A (1% locust bean gum), pts. | 100 | — | — | — | — | — |
| Blend B (3% locust bean gum), pts. | — | 100 | — | — | — | — |
| Blend C (5% locust bean gum), pts. | — | — | 100 | 100 | 100 | 100 |
| Locust bean gum, pts. | 5 | 5 | 5 | 5 | 5 | 5 |
| Magnesium stearate, pts. | 1.5 | 1.5 | 1.5 | 1.5 | 1.5 | 1.5 |
| Monocalcium phosphate, pts. | 5 | 5 | 5 | 10 | 15 | 20 |
| Disintegration time, min. | 1 | 3 | 10+ | 10 | 8 | 10+ |

Each of the direct compression vehicles of the foregoing examples can be blended in accordance with the following recipes and compressed to form tablets or wafers.

A. CONFECTIONERY TABLETS OR WAFERS
1. LEMON FLAVORED confectionery tablet:
    25.0 pts. direct compression vehicle
    75.0 pts. agglomerated sugar
    1.0 pt. citric acid, dry
    0.25 pt. encapsulated lemon flavor
    0.10 pt. yellow color No. 5
    1.0 pt. magnesium stearate
2. GRAPE FLAVORED confectionery tablet:
    50.0 pts. direct compression vehicle
    50.0 pts. agglomerated sugar
    2.0 pts. tartaric acid 0.25 pt. grape flavor
0.05 pt. grape color
0.5 pt. calcium stearate
3. CHERRY FLAVORED confectionery tablet:
   75.0 pts. direct compression vehicle
   25.0 pts. agglomerated sugar
   2.0 pts. fumaric acid
   0.2 pt. cherry flavor
   0.1 pt. red color
   1.0 pt. magnesium stearate B. PHARMACEUTICAL FORMULATIONS
1. 50.0 pts. direct compression vehicle
   37.5 pts. aluminum hydroxide
   1.0 pt. magnesium stearate
2. 100.0 pts. direct compression vehicle
   25.0 pts. calcium carbonate
   5.0 pts. magnesium carbonate
   1 drop peppermint oil
   2.0 pts. magnesium stearate
3. 100.0 pts. direct compression vehicle
   25.0 pts. acetyl salicylic acid
   15.0 pts. corn starch
   2.0 pts. magnesium stearate
4. 90.0 pts. direct compression vehicle
   10.0 pts. vitamin C in dry form
   2.0 pts. magnesium stearate Other active ingredients of use in blends with the direct compression vehicle are: sodium bicarbonate, acetanilid, phenecetin and magnesium trisilicate.

C. SPECIALTY PRODUCTS
1. INVERTASE TABLET
   96.4 pts. direct compression vehicle
   3.6 pts. liquid triple strength invertase (K=0.9)
   1.0 pt. magnesium stearate
2. COCOA-SUGAR TABLET
   35.0 pts. direct compression vehicle
   55.0 pts. agglomerated sugar
   10.0 pts. high fat cocoa
   0.2 pt. dendritic salt
   1.0 pt. magnesium stearate After blending, the mixture is tabletted to form a cocoa-sugar tablet.

3. HIGHLY CONCENTRATED COLOR TABLET
   90.0 pts. direct compression vehicle
   10.0 pts. dried yellow FD&C No. 6
4. YEAST FOOD TABLET
   34.0 pts. calcium sulfate ($2H_2O$)
   23.0 pts. flour
   9.0 pts. ammonium chloride
   0.25 pt. potassium bromate
   17.75 pts. sodium dihydrogen phosphate
   16.0 pts. salt
   900.0 pts. direct compression vehicle
   10.1 pts. magnesium stearate

What is claimed is:
1. A particulate composition useful as a direct compression vehicle for forming tablets consisting essentially of a dry mixture of:
   a. About 100 parts by weight of an intimate co-dried blend of a minor but effective portion of locust bean gum comprising at least about 0.5 weight per cent of said co-dried blend and a major portion of tricalcium phosphate;
   b. Up to about 200 parts of granular tricalcium phosphate as a diluent for said blend and in an amount sufficient to increase the incidence of picking in the absence of a lubricant; and
   c. Locust bean gum in an amount of from about 5 to about 15 weight per cent, based upon said co-dried blend and from about 3 to about 7 weight per cent, based upon the combined weight of said co-dried blend and granular tricalcium phosphate.

* * * * *